United States Patent
Kobayashi et al.

(10) Patent No.: US 7,513,253 B2
(45) Date of Patent: Apr. 7, 2009

(54) LIQUID MEDICATION CARTRIDGE AND INHALER USING THE CARTRIDGE

(75) Inventors: Masaya Kobayashi, Yokohama (JP); Kenichi Sekine, Kodama-gun (JP); Toshiyuki Nobutani, Yokohama (JP); Mitsuru Imai, Chichibu (JP)

(73) Assignee: Canon Kabushiki Kaisha, Tokyo (JP)

( * ) Notice: Subject to any disclaimer, the term of this patent is extended or adjusted under 35 U.S.C. 154(b) by 522 days.

(21) Appl. No.: 10/566,429

(22) Filed: Jan. 31, 2006

(65) Prior Publication Data

US 2007/0240706 A1 Oct. 18, 2007

Related U.S. Application Data

(63) Continuation of application No. PCT/JP2005/014361, filed on Jul. 29, 2005.

(30) Foreign Application Priority Data

Aug. 2, 2004 (JP) .............................. 2004-225510

(51) Int. Cl.
*A61M 15/00* (2006.01)
*B43K 5/02* (2006.01)
*B43K 5/14* (2006.01)

(52) U.S. Cl. .......................... 128/203.21; 128/200.12; 128/200.14; 128/200.16; 128/203.12; 401/132; 401/133; 401/134

(58) Field of Classification Search ............ 128/200.12, 128/200.11, 200.14, 200.24, 203.21, 203.19, 128/202.26, 203.12; 401/132, 133, 134
See application file for complete search history.

(56) References Cited

U.S. PATENT DOCUMENTS

| | | | | |
|---|---|---|---|---|
| 4,648,393 | A * | 3/1987 | Landis et al. | 128/200.23 |
| 5,497,763 | A | 3/1996 | Lloyd et al. | 128/200.14 |
| 5,692,492 | A | 12/1997 | Bruna et al. | |
| 5,894,841 | A | 4/1999 | Voges | 128/203.12 |
| 5,896,143 | A | 4/1999 | Matsui et al. | 347/24 |
| 6,196,218 | B1 * | 3/2001 | Voges | 128/200.14 |
| 6,196,219 | B1 * | 3/2001 | Hess et al. | 128/200.21 |
| 6,629,524 | B1 * | 10/2003 | Goodall et al. | 128/200.14 |
| 6,637,430 | B1 * | 10/2003 | Voges et al. | 128/200.14 |

(Continued)

FOREIGN PATENT DOCUMENTS

EP 684851 A1 4/1998

(Continued)

OTHER PUBLICATIONS

JP 2003-290356 A, Oct. 14, 2003; Machine translation provided by the Japanese Patent Office, entire document.*

(Continued)

*Primary Examiner*—Justine R Yu
*Assistant Examiner*—Clinton Ostrup
(74) *Attorney, Agent, or Firm*—Fitzpatrick, Cella, Harper & Scinto (57) ABSTRACT

A liquid medication cartridge includes an accommodating portion for accommodating a liquid medication; a liquid discharge portion having a discharge port for discharging the liquid medication by using an ink jet technique, a communicating member for establishing communication between the accommodating portion and the liquid discharge portion and a filling member for filling the liquid discharge portion with the liquid medication.

4 Claims, 9 Drawing Sheets

U.S. PATENT DOCUMENTS

| | | | |
|---|---|---|---|
| 2004/0178106 A1 * | 9/2004 | Morita | 206/459.1 |
| 2007/0062520 A1 | 3/2007 | Nobutani et al. | 128/200.14 |

FOREIGN PATENT DOCUMENTS

| | | |
|---|---|---|
| JP | 8-506746 A | 7/1996 |
| JP | 8-511966 | 12/1996 |
| JP | 3311039 | 5/2002 |
| JP | 3375637 | 11/2002 |
| JP | 2003-290356 A | 10/2003 |
| JP | 2004-290593 | 10/2004 |
| JP | 2004-290593 A | 10/2004 |
| WO | 94/19040 A1 | 9/1994 |
| WO | WO 95/01137 | 1/1995 |

OTHER PUBLICATIONS

PCT International Search Report mailed Nov. 22, 2005, for International Application No. PCT/JP2005/014361.

Written Opinion mailed Feb. 22, 2007 issued in counterpart application.

* cited by examiner

LIQUID MEDICATION CARTRIDGE AND INHALER USING THE CARTRIDGE

This application is a continuation of International Application No. PCT/JP2005/014361, filed Jul. 29, 2005, which claims the benefit of Japanese Patent Application No. 2004-225510, filed Aug. 2, 2004.

BACKGROUND OF THE INVENTION

1. Field of the Invention

The present invention relates to a liquid medication cartridge to be used in a device like an inhaler that discharges a medication as droplets. In particular, the present invention is suitable for use in an inhaler that discharges a liquid medication or a palatable substance, such as aroma or nicotine, in fine droplets for the user to inhale.

2. Related Background Art

Conventionally, as liquid discharge head tanks for ink jet recording, a number of products have been proposed in which a mechanism for filling a liquid discharge head with ink is provided on the printer main body side. For example, JP 3311039 B discloses an ink jet recording apparatus which has a suction means, a suction cap, and a protective cap and in which a discharge port is covered with a cap when no recording is being performed.

Recently, as an application of such ink jet technique, there has been developed a device in which liquid droplets containing a predetermined amount of medication are atomized in the device, and inhaled by the user through a mouthpiece (see, for example, JP 8-511966 A).

JP 3375637 B discloses a disposable package including a porous film and a container.

Further, JP 2004-290593 A discloses, as a liquid droplet discharge device, a package equipped with a recovery (filling) means. The recovery (filling) operation is conducted when placing the package in position in an inhaler.

SUMMARY OF THE INVENTION

In conventional ink jet recording apparatuses, an ink suction mechanism is provided on the recording apparatus main body side for the purpose of filling the liquid discharge portion with ink. In this ink suction mechanism, the liquid discharge portion is filled with ink by utilizing negative pressure obtained by a pump. In this process, it is rather difficult to control the ink filling amount by the negative pressure obtained by the pump, so that ink is sucked making allowance for a shortage of ink. The ink sucked is absorbed by an absorbing member installed in the recording apparatus main body.

On the other hand, in an inhaler to be used in the field of medical treatment when effecting lung inhalation of a liquid medication in the form of a mist, a container with the medication therein is opened to the atmospheric air immediately before use, i.e., inhalation. Conventional liquid medication cartridges with a liquid discharge portion utilizing the ink jet technique have the following problems:

1. In the case in which an absorbing means, such as a sponge, is provided in the inhaler and in which the liquid medication is sucked and retained in the inhaler, the liquid medication retained is allowed to be oxidized, which leads to a problem in terms of hygiene and odor.

2. An inhaler is mostly used three times or more a day, so that it is absolutely necessary for the inhaler to be able to be carried about. In the case of a portable type inhaler, however, the ink suction mechanism leads to an increase in the weight, a complicated construction, and an increase in the cost of the device.

In view of the above problems, it is an object of the present invention to provide a liquid medication cartridge and an inhaler which are easily portable and are of simple construction.

After careful study to solve the above problems in the prior art, the present inventors have succeeded in completing the present invention.

That is a liquid medication cartridge (CRG) according to the present invention is characterized by including: an accommodating portion for accommodating a liquid medication; a liquid discharge portion having a discharge port for discharging the liquid medication by using an ink jet technique; a communicating means for establishing communication between the accommodating portion and the liquid discharge portion; and a filling means for filling the liquid discharge portion with the liquid medication.

According to the present invention, the liquid discharge portion is filled with the liquid medication by the filling means provided in the liquid medication cartridge, whereby the filling operation is completed easily and a state allowing discharge can be attained. Due to this arrangement, there is no need to provide a complicated filling means in the device to be used, and a reduction in weight can be achieved, which helps to contribute to an improvement in the portability of the device. Further, the liquid medication cartridge is of a simple construction and easy to manufacture. Further, it can retain the liquid medication in a hermetically sealed state like a medication container on the market, whereby it is also possible to secure a long preservation period for the liquid medication.

DESCRIPTION OF THE PREFERRED EMBODIMENTS

In the following, the present invention will be described in detail.

The present invention provides a liquid medication cartridge having an ink jet type liquid discharge portion, characterized in that there is provided a means for filling the liquid discharge portion with the liquid medication.

In particular, the filling can be effected manually, so that the user can perform the filling operation immediately before use. Further, it is possible to fill the liquid discharge portion with liquid medication after establishing communication between a hermetically sealed accommodating portion and the liquid discharge portion. Due to the construction of the present invention, it is possible to realize a liquid medication filling operation with a simple construction in a liquid medication cartridge using the ink jet system.

That is, a liquid medication cartridge according to the present invention includes:

1) an accommodating portion for accommodating a liquid medication;
2) a liquid discharge portion having a discharge port for discharging the liquid medication by using an ink jet technique;
3) a communicating means for establishing communication between the accommodating portion and the liquid discharge portion; and
4) and a filling means for filling the liquid discharge portion with the liquid medication.

1) Accommodating Portion for Accommodating Liquid Medication

The accommodating portion (container) accommodates a liquid medication and maintains a highly sterilized condition therein, so that it is desirable to avoid as much as possible intrusion of foreign matter into the accommodating portion to reduce the contact area between the liquid medication and the foreign matter. In view of this, it is desirable to accommodate no such absorbing member as used in an ink jet recording apparatus for the purpose of retaining ink in the tank, and to accommodate the liquid medication alone. Among liquid medications, proteins, etc., are particularly subject to degeneration, so that special care is required in this regard.

It is desirable for the accommodating portion to be formed of a resin material involving no elution of impurities into the liquid medication and not affecting living bodies. Examples of resin materials that can be used include discrete resins, such as polyethylene, soft polypropylene, polycarbonate, ABS resin, and methacrylate resin, and composite resins, such as polyethylene/eval (EVAL: ethylene vinyl alcohol copolymer, registered trademark of Kurashiki Rayon), and polypropylene/eval. It is desirable for the portions other than the accommodating portion, which are brought into contact with the liquid medication, e.g., the communicating means, to be formed of the same material as the container.

2) Liquid Discharge Portion with Discharge Port for Discharging Liquid by Ink Jet Technique The liquid discharge portion of the present invention is an ink jet head capable of discharging liquid in the form of droplets by using the ink jet technique. In particular, it is desirable to adopt a bubble jet system, in which a heater element is provided behind the discharge port to heat the liquid to generate bubbles by film boiling, discharging liquid droplets by the bubbling energy. In this construction, a large number of discharge nozzles can be easily formed.

Apart from this, it is also possible to adopt a construction in which a piezo-oscillation element is provided behind the discharge port to discharge a multitude of liquid droplets by utilizing oscillation energy.

Further, the liquid discharge head as disclosed in JP 2003-154655 A is also preferable.

3) Communicating Means for Establishing Communication Between Accommodating Portion and Liquid Discharge Portion The communicating means for establishing communication between the accommodating portion and the liquid discharge portion, which are disconnected from each other prior to use, establishes communication therebetween at the time of use. Two forms are possible for the communicating means.

In the first form, a part of the accommodating portion (container) is formed of a film easy to pierce, which is pierced by a member of a sharp configuration at the time of use. The member of a sharp configuration may be provided on the container side, or on the liquid discharge portion side.

In the second form, the communication passage between the accommodating portion and the liquid discharge portion is formed of a deformable material, and a blocking object is pressed against it with pressure to stop the communication passage; at the time of use, the pressure is reduced and the blocking object is removed, thereby securing communication.

4) Filling Means for Filling Liquid Discharge Portion with Liquid Medication

The filling means for filling the liquid discharge portion with liquid medication is formed, for example, as follows: at least a part of the accommodating portion (container) is formed in a deformable structure, and the deformable portion is pressed to thereby reduce the inner volume of the accommodating portion. The pressing of the deformable portion may be effected by a special member or directly by a human finger.

Alternatively, it is also possible to adopt a construction in which the accommodating portion (container) has no deformable portion and in which the communicating means enters the accommodating portion to displace the liquid medication therein.

When effecting the filling, it is necessary to remove the bubbles in the liquid discharge portion to a degree that the discharge is not affected, so that it is necessary for the liquid medication to overflow to some extent on the surface of the liquid discharge portion. The liquid medication cartridge of the present invention is of a construction in which liquid is discharged by applying a discharge force to the liquid in the liquid discharge portion, so that a deformation of the accommodating portion by a volume large enough to fill the liquid discharge portion with liquid medication serves the purpose. Once the bubbles in the liquid discharge portion have been removed to a sufficient degree, it is possible to discharge the liquid filling the liquid discharge portion by supplying electricity to the heater element or piezo element in the liquid discharge portion.

In view of the fact that the liquid medication cartridge is disposable, the liquid medication cartridge of the present invention is inexpensive and of a simple construction. Further, the filling operation is to be conducted by hand. In view of this, it is necessary to take the balance between accuracy and liquid medication cost into consideration in determining the amount by which the liquid medication is caused to overflow from the surface of the liquid discharge portion.

The present inventor conducted an examination in which (1) the number of discharge ports in the liquid discharge portion, (2) the size of the accommodating portion, (3) the communicating means, and (4) the filling means were varied. The results of the examination have shown that, from a practical point of view, no problem is involved if the volume of liquid medication overflowing from the surface of the liquid discharge portion is 15% or more of the volume of the container accommodating the liquid medication; generally speaking, if the volume of liquid medication overflowing is 20% of the volume of the container, it is generally possible to discharge liquid medication through all of the discharge ports. Of course, it goes without saying that, as long as a satisfactory discharge state can be attained, the less the volume of liquid medication allowed to overflow, the more desirable it is.

In the case of an accommodating portion of the type in which a part of the container has a deformable portion, the sum total of the volume of liquid medication overflowing when filling the liquid discharge portion with the liquid medication in the accommodating portion and the inner volume from the communicating portion to the liquid discharge portion, is substantially equal to the deformation volume of the accommodating portion (container).

Further, it has been found out that the inner volume from the communicating portion to the liquid discharge portion may be 10 to 20% of the inner volume of the accommodating portion.

Thus, when the deformation volume of the accommodating portion is 40% of the inner volume of the accommodating portion, it is possible to attain a state in which liquid discharge is possible by causing liquid medication to overflow from the surface of the liquid discharge portion by an amount corresponding to 20% of the inner volume of the accommodating portion when filling the liquid discharge portion with liquid medication from the communicating portion. From a practical point of view, it is only necessary for the deformation volume of the accommodating portion to be 25% or more of the inner volume of the accommodating portion.

An inhaler equipped with a liquid medication cartridge according to the present invention preferably includes a mouthpiece with an inhaling port enabling the user to inhale medication, a casing connected to the mouthpiece, a liquid medication cartridge for discharging liquid within the casing, and a control means for controlling the liquid discharge portion. When the inhaler equipped with a liquid medication cartridge is formed as a portable device, the inhaler also preferably contains a battery. Further, more preferably, there is provided a detecting means (a negative pressure sensor, etc.) for detecting inhalation by the user, so that discharge can be effected upon inhalation.

EMBODIMENTS

In the following, specific embodiments of the liquid medication cartridge of the present invention will be described. In all of the following embodiments, the liquid medication cartridge is composed of the following four components:
1) an accommodating portion for accommodating a liquid medication;
2) a liquid discharge portion having a discharge port for discharging the liquid medication by using an ink jet technique;
3) a communicating means for establishing communication between the accommodating portion and the liquid discharge portion; and
4) a filling means for filling the liquid discharge portion with the liquid medication.

Further, in the following embodiments, the liquid discharge portion is brought into a state in which discharge is possible by successively conducting the following two operations.

The first operation is the operation of establishing communication between the accommodating portion and the liquid discharge portion, which have been disconnected from each other, by using the communicating means.

The second operation is the operation of filling the liquid discharge portion with liquid medication to bring it to a state in which discharge is possible.

In the following embodiments, the communication and filling in the liquid medication cartridge will be described in detail with reference to FIGS. 1 through 4.

Embodiment 1

Figure 1A:
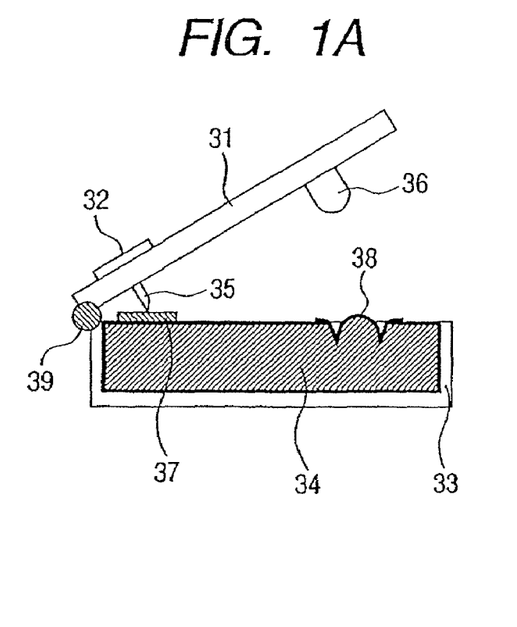
FIG. 1A is a sectional view of a liquid medication cartridge with a hinge in a state prior to establishment of communication and filling.
Figure 1B:
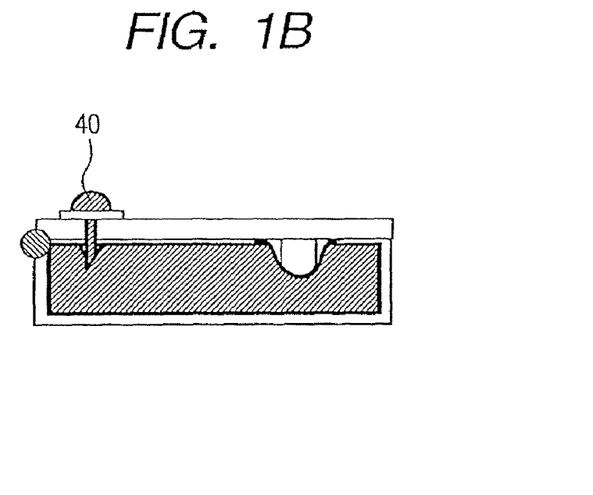
FIG. 1B is a sectional view of a liquid medication cartridge with a hinge in a state after establishment of communication and filling.

FIG. 1A is a sectional view of a liquid medication cartridge according to the present invention in which communicating operation and filling operation can be successively conducted by utilizing a hinge 39. The drawing shows the liquid medication cartridge in a state prior to establishment of communication and filling. FIG. 1B shows the liquid medication cartridge of the present invention in a state after establishment of communication and filling. A base plate 31 and a container 33 are integrated through the intermediation of the hinge 39. By molding them as a single part, it is possible to achieve a reduction in the number of parts and a reduction in cost. Provided on the base plate 31 are a liquid discharge portion 32 and a protrusion 36 constituting the filling means. The liquid discharge portion 32 communicates with a communicating means 35 within. The liquid medication is accommodated in the container 33, to which a film 37 and a deformable diaphragm 38 are mounted.

The film 37 is thin enough to be pierced by the communicating means 35, and is required to exhibit a high oxygen gas barrier property and steam barrier property from the viewpoint of the preservation of the liquid medication. The film preferably consists of an aluminum deposition film, a silica deposition film, a film formed by sandwiching eval between polyethylene or polypropylene layers, etc. Regarding the material of the diaphragm, it is desirable to adopt polyethylene, polypropylene, etc. in conformity with the material of the container. When the requisite oxygen gas barrier property and steam barrier property cannot be secured, it is also possible to adopt a form in which the liquid medication cartridge is externally packaged to secure the requisite barrier property.

In the first operation, the base plate 31 is rotated around the hinge 39 to move along an arc toward the container 33. The communicating means 35 pierces the film 37, whereby communication is established between the liquid discharge portion 32 and the container 33.

In the second operation, the base plate 31 is brought closer to the container 33, with the result that the filling means 36 presses the diaphragm 38. As a result, the diaphragm 38 undergoes deformation, and liquid medication 34 in an amount corresponding to the deformation volume of the diaphragm 38 is transferred through the communicating means 35 to fill the liquid discharge portion 32. If bubbles remain in the vicinity of the heater element within the liquid discharge portion 32, discharge cannot be conducted, so that it is necessary to cause some liquid medication to overflow from the surface of the liquid discharge portion 32 (as indicated at 40). When the liquid medication that has overflowed is allowed to stay, discharge of droplets is impossible, so that it is necessary to wipe off the surface of the liquid discharge portion 32 to remove the surplus liquid medication.

In some cases, the discharge of liquid medication can be conducted smoothly by providing a port communicating with the atmospheric air (not shown).

After the establishment of communication, a careful examination was conducted on the ratio of the volume of the liquid medication overflowing from the surface of the liquid discharge portion at the time of filling, and the ratio of deformation of the container by varying (1) the number of discharge ports in the liquid discharge portion, (2) the volume of the liquid discharge portion and the communicating portion, and (3) the volume of the container. The results obtained are shown in Table 1. As for the discharge check after the filling, the cases in which discharge was possible through all the nozzles are indicated by symbol ⊚ (no problem), the cases in which the ratio of the nozzles through which discharge was impossible was 10% or less of all the nozzles are indicated by symbol ○ (no problem from the practical point of view), and the cases in which the ratio of the nozzles through which discharge was impossible exceeded 10% of all the nozzles are indicated by symbol Δ (problematic).

It can be seen from Table 1 that, for liquid medication to be discharged through all the nozzles, it is necessary to increase the volume of liquid medication overflowing from the liquid discharge portion at the time of filling according to the nozzle number ratio (the discharge port number ratio). It goes without saying that, when the overflow volume (a) is constant, the overflow ratio (a/c) decreases if the container volume (c), that is, the inner volume of the accommodating portion is increased. Although it depends on the nozzle number ratio, no problem is involved from the practical point of view when the overflow ratio is 15%; when the overflow ratio is 20%, it is possible to effect discharge through all the nozzles. Regarding the deformation ratio, no problem is involved from the practical point of view when the deformation ratio is 25%; when the deformation ratio is 30%, it is possible to effect discharge through all the nozzles. Even if the case in which the container volume is small is taken into consideration, it seems that discharge can be reliably effected through all the nozzles when the deformation ratio is 40%. This ratio remained the same in the other embodiments, too.

It should be noted that, in suppressing an increase in liquid medication cost, it is desirable to design the cartridge such that the overflow volume is as small as possible within the range in which a desired discharge condition can be realized according to the number of nozzles and the container volume.

Embodiment 2

Figure 2A:
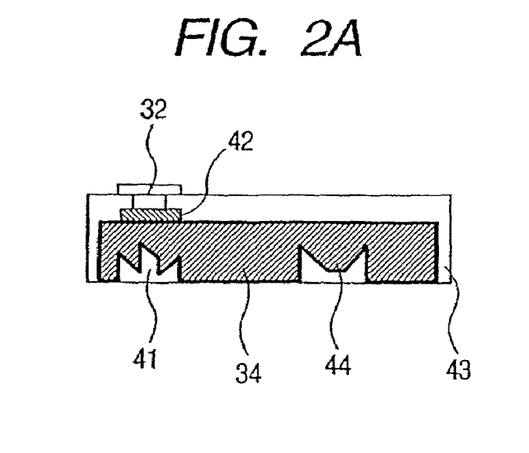
FIG. 2A is a sectional view of a liquid medication cartridge having a communicating means on the accommodating portion side in a state prior to establishment of communication and filling.
Figure 2B:
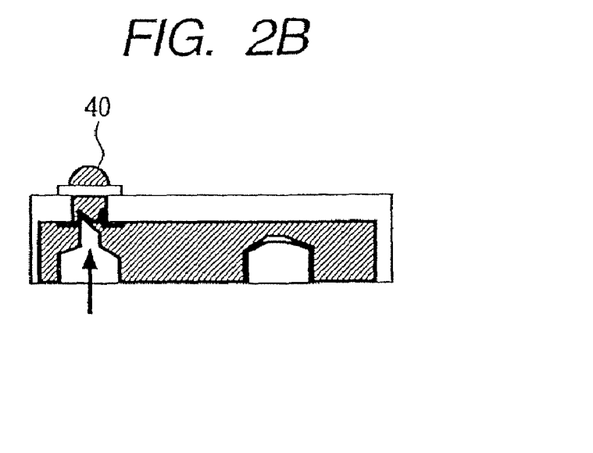
FIG. 2B is a sectional view of a liquid medication cartridge having a communicating means on the accommodating portion side in a state after establishment of communication and filling.

FIG. 2A is a sectional view of a liquid medication cartridge according to the present invention having the communicating means on the container side in a state prior to establishment of communication and filling. FIG. 2B is a sectional view of the liquid medication cartridge of the present invention in a state after establishment of communication and filling. The liquid medication in a container 43 and the liquid discharge portion 32 are isolated from each other through the intermediation of a film 42. As a communicating means 41, there is provided a component of a sharp configuration, for example, a needle-like component. The communicating means 41 and a diaphragm 44 are preferably formed of a soft material that can be deformed by pressurization by a finger, and they must be formed of a material that can maintain shape retention property. A material that can maintain shape retention property

TABLE 1

Ratio of Overflowing Liquid Medication and Ratio of Container Deformation at the Time of Liquid Medication Filling Operation

| Ratio of the number of discharge ports in the liquid discharge portion | Overflow volume (a) | Volume (b) of the discharge portion and the communicating portion | Container volume (c) | Deformation volume (a + b) | Overflow ratio (a/c) | Deformation ratio (a + b)/c | Discharge check after filling |
|---|---|---|---|---|---|---|---|
| 1 | 3 | 20 | 130 | 23 | 2% | 18% | Δ |
| 1 | 10 | 20 | 130 | 30 | 8% | 23% | ⊚ |
| 1 | 5 | 20 | 100 | 25 | 5% | 25% | ○ |
| 1 | 5 | 10 | 100 | 15 | 5% | 15% | ○ |
| 1 | 10 | 20 | 100 | 30 | 10% | 30% | ⊚ |
| 1 | 3 | 10 | 50 | 13 | 6% | 26% | Δ |
| 1 | 10 | 10 | 50 | 20 | 20% | 40% | ⊚ |
| 2 | 15 | 20 | 100 | 35 | 15% | 35% | ⊚ |
| 3 | 3 | 10 | 100 | 13 | 3% | 13% | Δ |
| 3 | 5 | 10 | 100 | 15 | 5% | 15% | Δ |
| 3 | 10 | 10 | 100 | 20 | 10% | 20% | Δ |
| 3 | 15 | 10 | 100 | 25 | 15% | 25% | ○ |
| 3 | 20 | 10 | 100 | 30 | 20% | 30% | ⊚ | maintains its shape if no pressure is applied after its deformation by pressurization by a finger.

While in the above embodiment establishment of communication and filling are effected through pressurization by a finger of the user, this should not be construed restrictively. It is also possible for the communicating operation of the communicating means to be mechanically effected by, for example, controlling the pressurization of the diaphragm by a pressurizing means electrically connected to a control means.

In the first operation, the film 42 is pushed open by pushing the communicating means 41 by a finger, establishing communication between the liquid discharge portion 32 and the container 34.

In the second operation, the liquid discharge portion 32 is filled with liquid medication 34 through the communicating means 41 by an amount corresponding to the volume of the portion of the diaphragm 44 that undergoes deformation through pressing of the diaphragm 44 by a finger. As in Embodiment 1, the surface of the liquid discharge portion 32 is wiped off to remove the overflowing liquid medication 40.

Embodiment 3

Figure 3A:
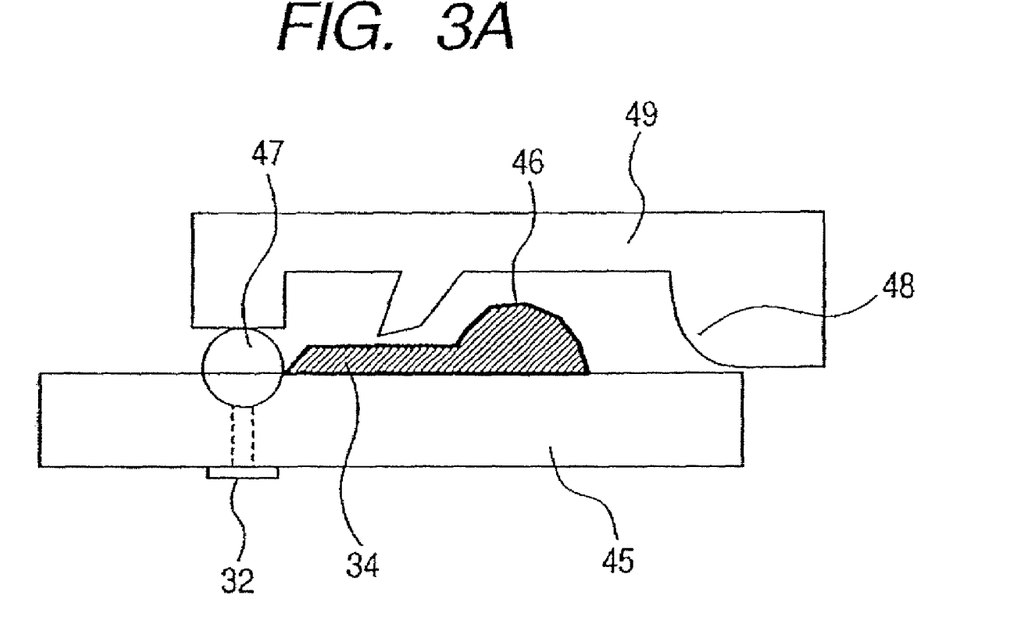
FIG. 3A is a sectional view of a liquid medication cartridge in a state prior to establishment of communication and filling, with an accommodating portion and a liquid discharge portion that originally communicate with each other being disconnected by a communicating means.
Figure 3B:
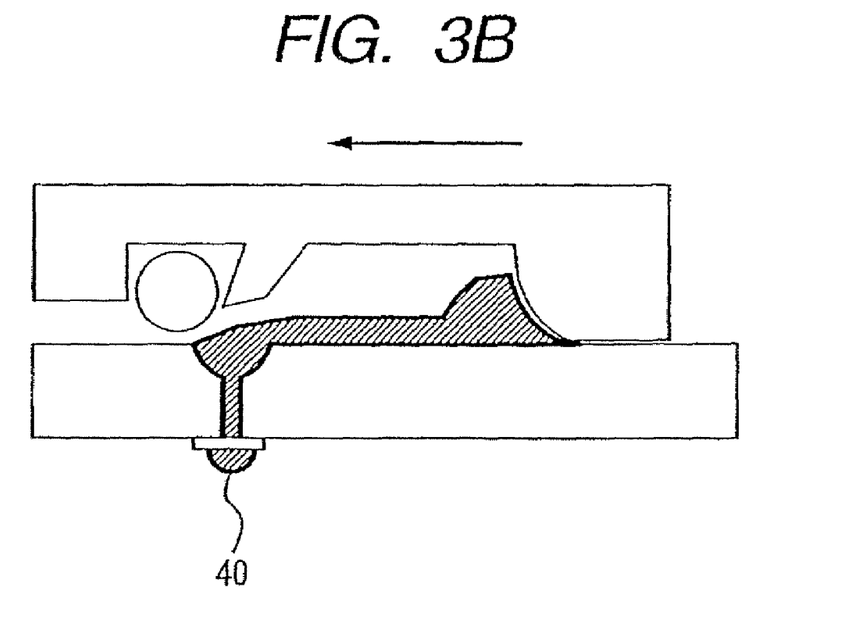
FIG. 3B is a sectional view of a liquid medication cartridge in a state after establishment of communication and filling, with the disconnection by the communicating means of the originally communicating accommodating portion and liquid discharge portion being canceled.

FIG. 3A is a sectional view of a liquid medication cartridge according to the present invention prior to establishment of communication and filling in a state in which the accommodating portion (container) and the liquid discharge portion, which originally communicate with each other, are disconnected from each other by a disconnecting means (pinch) 47. FIG. 3B is a sectional view of the same after establishment of communication and filling. A base plate 45 is equipped with a container 46 and the liquid discharge portion 32, and a slider 49 is slidably mounted to the base plate 45. The slider 49 is equipped with a means for pressing the disconnecting means 47 and a filling means 48 for effecting liquid medication filling. The liquid medication 34 is accommodated in the container 46, with the disconnecting means (pinch) 47 being pressed by the slider 49.

There are no particular limitations regarding the configuration and material of the disconnecting means (pinch) 47 as long as they allow canceling of communication. It may be formed in a spherical configuration as shown in FIG. 3A, or it may be formed in a wedge-like configuration. It is desirable for the container 46 to be formed of a flexible thin material that undergoes deformation as the amount of liquid medication 34 therein decreases.

In the first operation, the disconnecting means (pinch) 47 is released by causing the slider 49 to slide, and communication is established between the liquid discharge portion 32 and the container 46.

In the second operation, the slider 49 is caused to slide further to thereby press the container 46 with the filling means 48 to deform it, and the liquid medication 34 therein fills the liquid discharge portion 32. As in the above embodiments, the surplus, overflowing liquid medication 40 is removed by wiping off the surface of the liquid discharge portion 32.

Embodiment 4

Figure 4A:
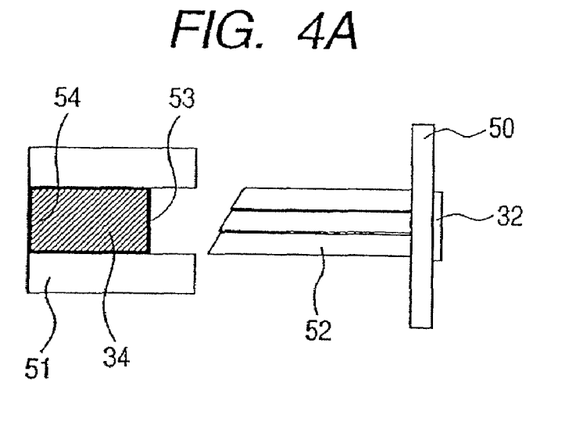
FIG. 4A is a sectional view of a liquid medication cartridge in which a communicating means also serves as a filling means in a state prior to establishment of communication and filling.
Figure 4B:
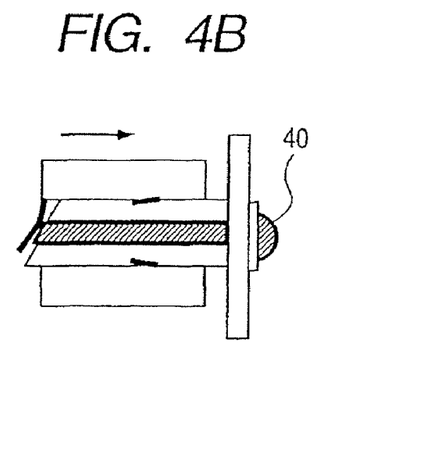
FIG. 4B is a sectional view of a liquid medication cartridge in which a communicating means also serves as a filling means in a state after establishment of communication and filling.

FIG. 4A is a sectional view of a liquid medication cartridge according to the present invention in which a communicating means 52 also serves as a filling means in a state prior to establishment of communication and filling. FIG. 4B is a sectional view of the liquid medication cartridge according to the present invention prior to establishment of communication and after filling. A base plate 50 is equipped with a communicating means 52 and the liquid discharge means 32.

Liquid medication 34 is accommodated in the container 51, and is cut off from the atmospheric air by a film 53 and a film 54. The requisite performance of the film 53 and the film 54 is the same as that of the film 37.

By making the volume of the communicating means 52 sufficiently large, the liquid medication 34 in the container 51 is pushed out at the time of establishment of communication, and fills the liquid discharge portion 32.

In the first operation, the communicating means 52 is pressed against the film 53 to break the same, thereby establishing communication between the liquid discharge portion 32 and the container 51.

In the second operation, the communicating means 52 is further pushed in, whereby the liquid medication 34 in the container 51 is pushed out and the liquid medication 34 fills the liquid discharge portion 32. By breaking the film 54 by the communicating means 52, an atmospheric air communication port is obtained. As in the above-described embodiments, the surplus, overflowing liquid medication 40 is removed by wiping off the surface of the liquid discharge portion 32.

While this embodiment employs the films 53, 54, the use of such films should not be construed restrictively; other means may be adopted as long as it can be broken by pushing in the communicating means 52. For example, it is also possible to mold the container 51 and the film 53 integrally by injection molding. The film 54 may be formed as a thin plate, which is detached by pressing the communicating means 52 against it.

EXAMPLE OF INHALER UTILIZING PRESENT INVENTION

An inhaler using a cartridge according to the present invention will be described in detail.

An inhaler or inhaling device according to an embodiment of the present invention is formed so as to be capable of being carried about by the user, and is equipped with a storage means for storing personal information on the user including information on the medical record and prescription of the user; the inhaler is capable of quantitative discharge of a liquid medication in the form of fine droplets of high uniformity in particle size, and enables the user to inhale the liquid medication. Further, in order for the user to inhale the liquid medication efficiently and hygienically according to the information on the prescription, a discharge head cartridge (CRG) unit, which is equipped with a mouthpiece with an inhaling port for the user to inhale and a tank (accommodating portion) for accommodating the liquid medication and which is adapted to discharge the liquid medication supplied from the tank in fine droplets, is detachably attached to the inhaler main body at the time of use.

Further, the flow passage forming the airflow in the entire inhaler is formed solely by the mouthpiece, and a throttle portion serving as a pressure mitigating means is provided at some midpoint in the mouthpiece; a pressure detecting portion is arranged on the user side (that is, the inhaling port side) of the throttle portion, and the discharge portion of the CRG unit is arranged on the atmospheric air intake port side of the throttle portion. A negative pressure higher than a fixed level (for example, −0.3 KPa or more (0.3 or more in absolute value)) is applied to the discharge head portion, liquid medication is allowed to flow out of the discharge port, and clogs the discharge port, with the result that the discharge of the liquid medication from that onward cannot be effected in a satisfactory manner. By providing the throttle portion, the discharge port does not directly receive the negative pressure generated through inhalation by the user, and the discharge of fine droplets through the discharge port of the discharge head can be effected continuously in a satisfactory manner. In this way, the discharge port of the discharge portion is arranged at a position where a pressure difference large enough to prevent the liquid medication from being discharged of itself through the discharge port due to the negative pressure, which is the pressure difference from the atmospheric pressure generated at the time of inhalation, making it possible to perform the discharge of liquid droplets in a satisfactory manner. The discharge system in the discharge portion may be one utilizing heat energy or piezoelectric energy. In either system, liquid supply is effected from the tank open to the atmospheric air by the capillary force of the nozzle, so that an atmospheric pressure environment is required which allows balancing between the (negative) pressure due to the tank and the discharge port meniscus.

Figure 12:
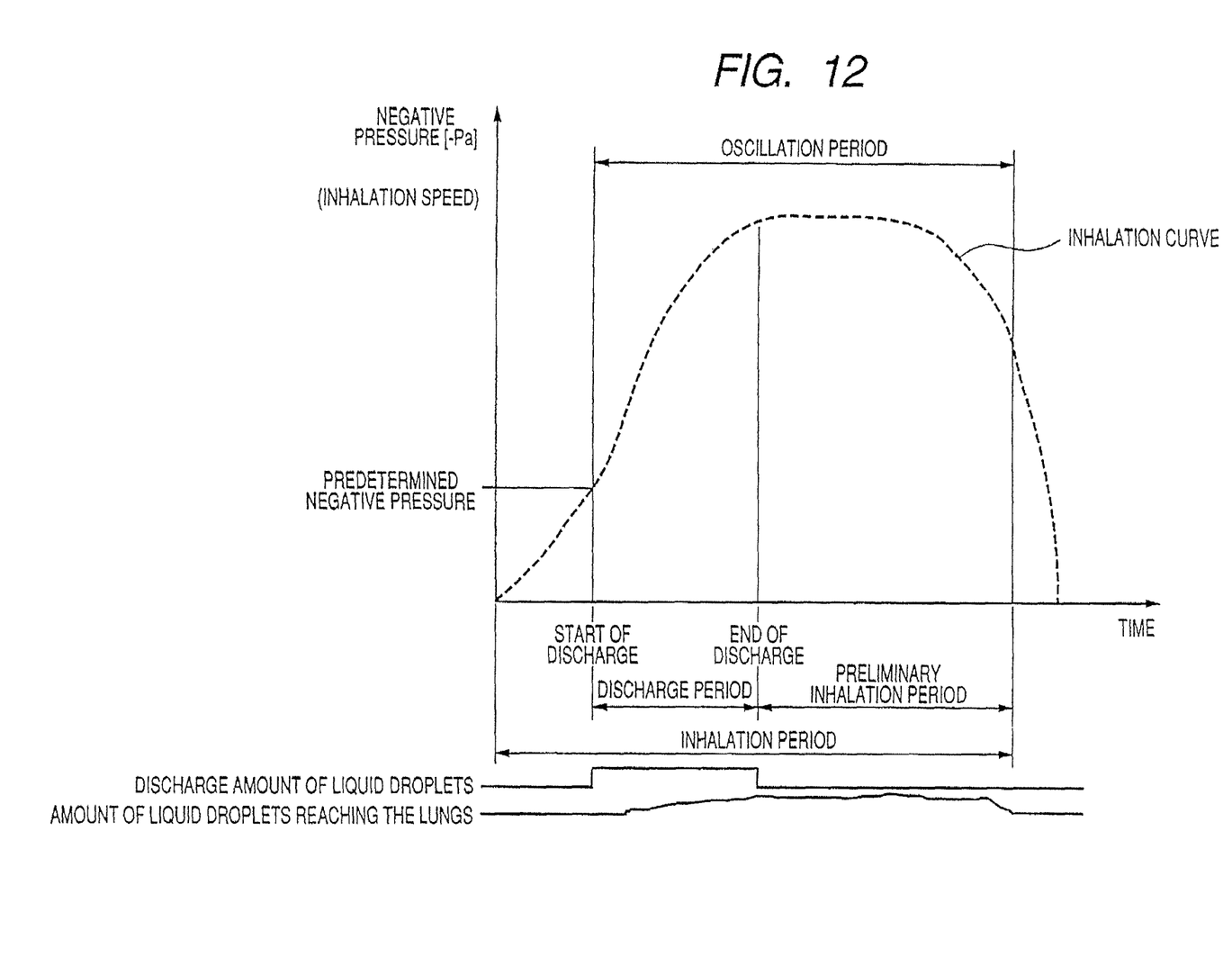
FIG. 12 is a graph illustrating an example of the inhaling operation of the inhaler or inhaling device of FIG. 5.

As shown in FIG. 12, the discharge from the discharge port is started upon detection of a fixed level of negative pressure by the pressure detecting portion; regarding the minimum negative pressure detected by the pressure detecting portion, it should be noted that the negative pressure detected by the pressure detecting portion differs from person to person according to the inhalation amount; generally speaking, it depends on the breathing capacity of the user, so that it has to be set appropriately. Thus, taking into consideration the case of a child or an aged person, whose breathing capacity is small, the sectional area of the throttle portion should be set at approximately 10 mm$^2$ so that this negative pressure may be −0.5 KPa or more (0.5 or more in absolute value), whereby it is possible to measure the changes in the negative pressure produced through inhalation (the inhalation curve shown in FIG. 12) accurately by the pressure detecting portion.

Here, the airflow in the entire inhaler is formed solely by the mouthpiece, so that the contamination of the airflow portion due to the liquid medication is restricted to the flow passage in the mouthpiece, so that the interior of the inhaler can be maintained in a safe and hygienic condition solely by cleaning the mouthpiece.

Further, when discharging the liquid medication from the inhaler, by varying the parameters related to the discharge of the liquid medication (discharge speed, discharge time, etc.) according, for example, to the inhalation amount (that is, by varying the parameters according to the changes in the inhalation curve shown in FIG. 12 detected by the pressure detecting portion), it is possible to send more liquid medication into the lungs of the user, thus enhancing the inhalation efficiency. In this way, in the case in which there is provided a discharge control means which varies the parameters related to the discharge of liquid medication according to the changes in the flow velocity (changes in the negative pressure) obtained by the negative pressure sensor within a predetermined period of time in which the user conducts inhalation, it is also possible to provide a means for demanding re-inhalation when the user has not been able to perform a predetermined inhalation within a predetermined period of time for the inhalation. This embodiment, which attaches importance to usability, reduces bothersome operation as much as possible, making it possible for anyone to use the inhaler anywhere with ease.

It is also possible to adopt the following construction.

As the pressure mitigating means, it is also possible to use a valve which normally substantially closes the flow passage forming the airflow and which opens at the time of inhalation; a pressure detecting portion is arranged on the inhaling port side of this valve, and the discharge port of the discharge portion is arranged on the opposite side thereof. The valve, which has been closed, starts to open upon inhalation, so that a mitigated negative pressure reaches with some delay the discharge port of the discharge portion on the opposite side of the inhaling port with respect to the valve, thus functioning as a pressure mitigating means.

It is also possible for the pressure detecting portion and the discharge port of the discharge portion to be arranged so as to face separate flow passages from the inhaling port. In this case, the flow passages form a flow passage outlet at the inhaling port, and the inhaling port is formed around the flow passage outlet in conformity with the configuration of a human mouth, and has a portion forming another flow passage, with the portion where the pressure detecting portion is arranged (the hole communicating with the negative pressure sensor) facing the other flow passages.

Further, it is also possible to provide a means which monitors the inhalation amount by using the negative pressure sensor (that is, monitors the inhalation curve shown in FIG. 12), letting the user know whether the inhalation amount has been of an appropriate value or not through blinking of an LED, a change in the oscillation mode of the oscillation motor, etc. Further, it is also possible to provide a means for letting the user know until when he or she is to perform the inhalation once started. As a means of thus informing the user of the requisite inhalation time, it is possible to use a means utilizing the oscillation of an oscillation motor.

In the inhaler thus constructed, the mental and physical burden on the patient (user) is relieved, and the inhalation of the medication (liquid medication) is possible through a simple operation by the patient; the discharge control of the medication is effected accurately according to the prescription, and the discharge drive parameters are varied according to the inhalation amount of the patient, whereby more medication is sent into the lungs, thus enhancing the inhalation efficiency and making it possible to give medication efficiently to the patient.

In the following, forms of the inhaler will be described in detail with reference to the drawings.

APPLICATION EXAMPLE 1

Figure 5:
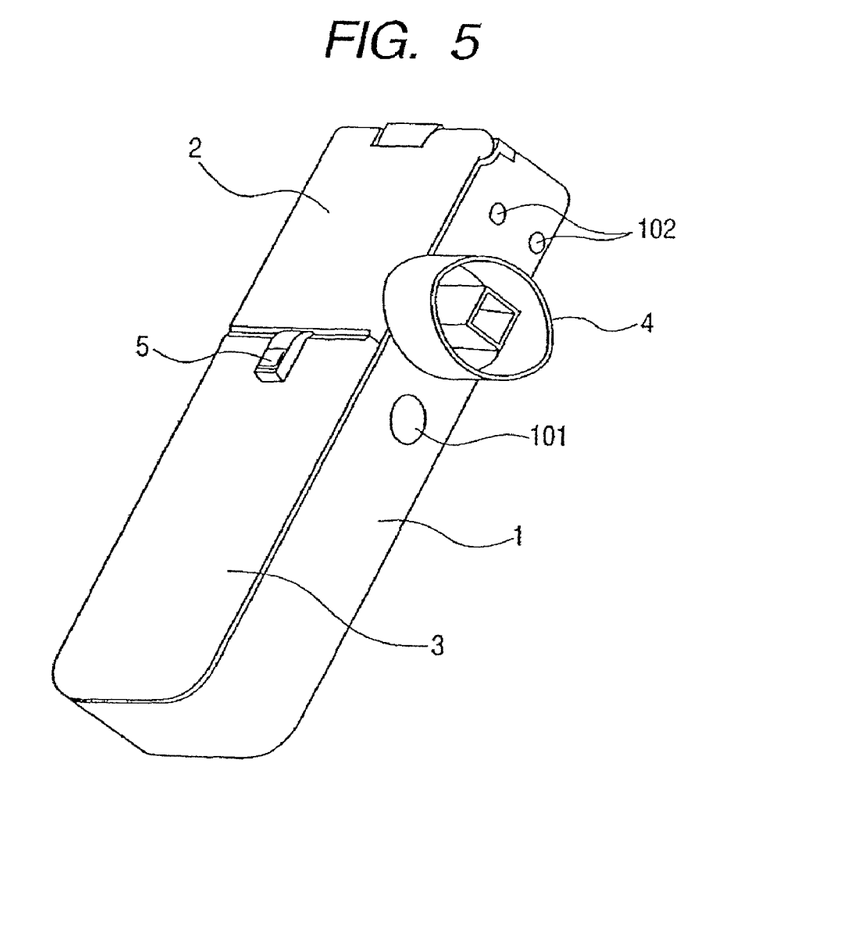
FIG. 5 is a perspective view of an example of an inhaler or inhaling device according to the present invention.

FIG. 5 is a perspective view of an outward appearance of an inhaler. Reference numeral 1 indicates the main body of the inhaler, reference numeral 2 indicates an access cover, and reference numeral 3 indicates a front cover. These components form a housing. Reference numeral 5 indicates a lock lever. In order that the access cover 2 may not be opened during use, it is formed such that a protrusion 2a provided at the forward end of the access cover 2 is caught by a claw-shaped portion provided at the forward end of the lock lever 5, which is urged by a spring. When the lock lever 5 is caused to slide downwards, the access cover 2 is opened around a hinge shaft (not shown) by the force of an access cover return spring (not shown) urging the access cover 2. Reference numeral 101 indicates a power source switch, and reference numeral 102 indicates display LEDs for indicating that the discharge head cartridge (CRG) unit described below or the mouthpiece has not been attached yet, or that the tank of the CRG unit is empty, etc.

Figure 6:
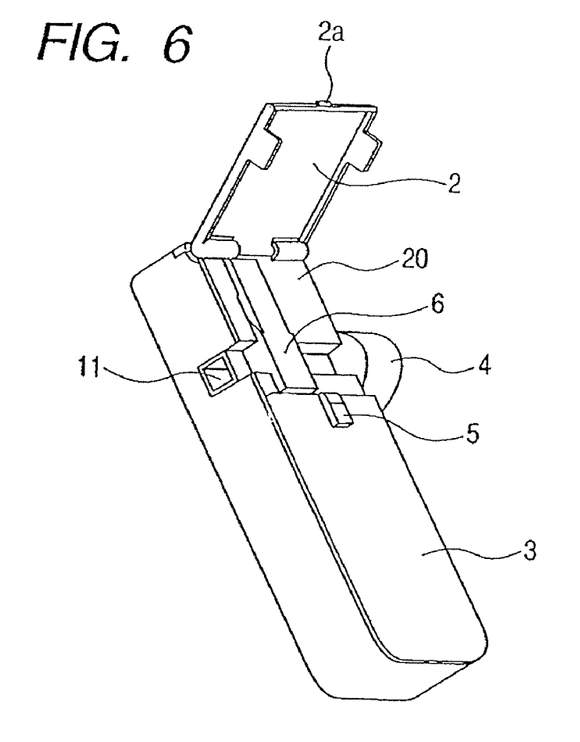
FIG. 6 is a perspective view of the inhaler of FIG. 5, with an access cover open.
Figure 7:
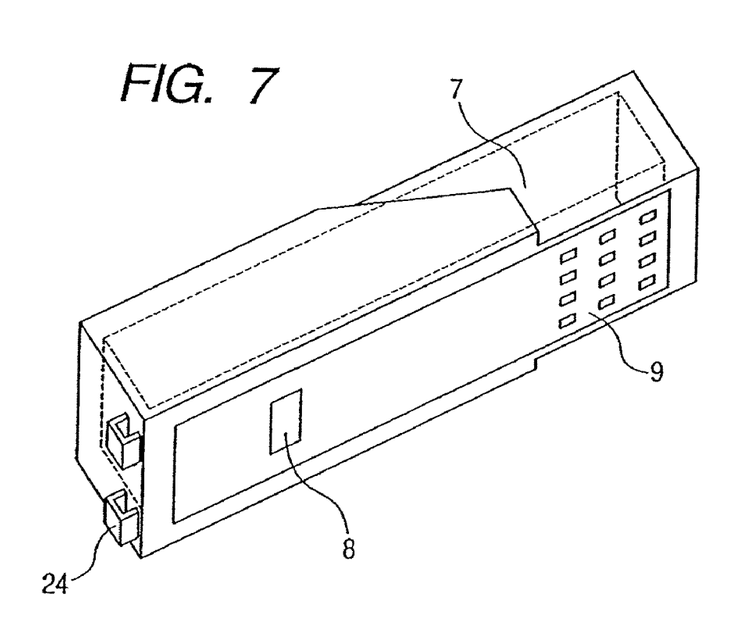
FIG. 7 is a perspective view of an example of a CRG unit.

FIG. 6 shows a state in which the access cover 2 is open. When the access cover 2 is opened, a CRG unit 6 attached in the housing along a CRG guide 20, and a mouthpiece 4 become visible. The mouthpiece 4 is under the CRG unit 6, and these components are attached so as to cross each other. FIG. 7 is an overall view of the CRG unit 6. The CRG unit 6 is composed of a tank 7 containing medication, a head portion (discharge portion) 8 for discharging the medication, a portion (electrical connection portion) 9 with an electrical connection surface for supplying from a battery 10 (see FIG. 11)

power for generating heat energy in a heater provided in the head portion 8, etc. The battery 10 can be charged as a secondary battery retaining within the inhaler the power for generating heat energy in the heater. The front surface portion of the CRG unit 6 can be opened around a hinge portion 24, allowing the access to the tank 7. A protrusion, for example, is formed on the back surface of the front surface portion, and simultaneously with the closing of the front surface portion, this protrusion enters the tank 7 to apply some pressure to the medication in the tank 7, thereby refreshing the discharge port of the head portion 8.

Figure 8:
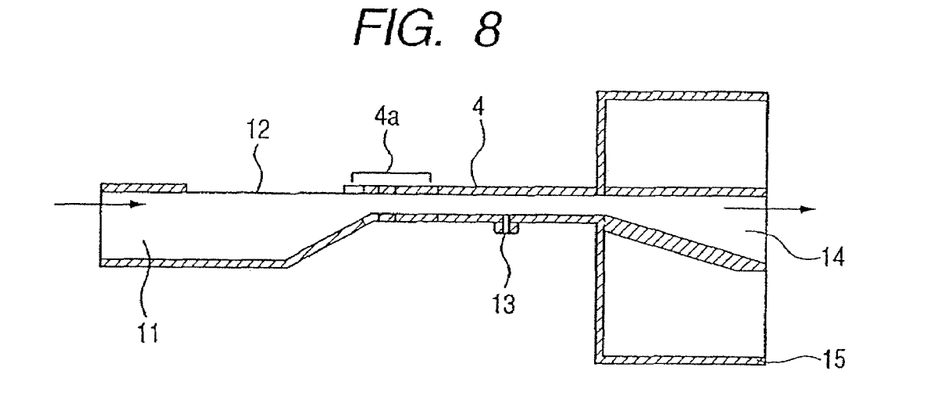
FIG. 8 is a side sectional view of an example of a mouthpiece.
Figure 9:
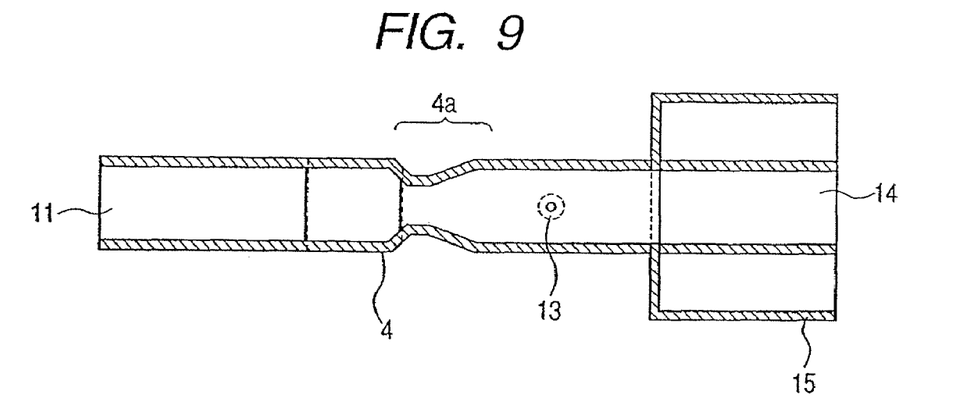
FIG. 9 is a front sectional view of the mouthpiece of FIG. 8.
Figure 10:
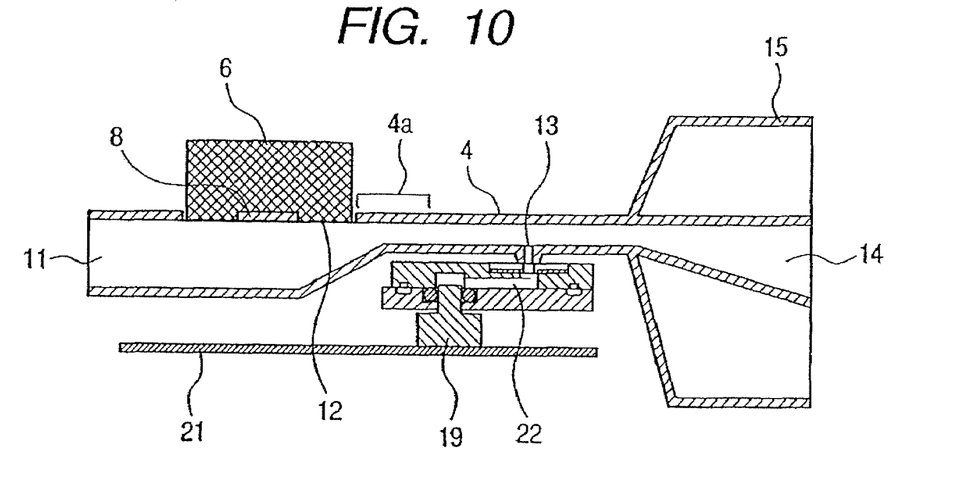
FIG. 10 is a side sectional view showing the positional relationship between the mouthpiece of FIG. 8, a negative pressure sensor, and a discharge head portion of a CRG unit.

FIGS. 8 and 9 are sectional views of the mouthpiece 4. In the mouthpiece 4, an air flow passage is formed by the mouthpiece 4 alone. In a portion near an air intake port 11, there is provided a window (liquid medication intake port) 12 for taking in liquid medication from the discharge port provided in the head portion 8 of the CRG unit 6. Halfway through the mouthpiece 4, there is formed a throttle portion 4a gently inclined so as to decrease in sectional area. As shown in detail in FIG. 10, in the portion where the sectional area increases again from the throttle portion 4a reduced in sectional area, there is provided a hole 13 communicating with a measurement hole of a negative pressure sensor 19 for detecting negative pressure to detect inhalation speed or flow rate as the integration value thereof. The negative pressure sensor 19 is arranged on a control board 21 (see FIGS. 10 and 11). Halfway through the flow passage providing communication between the air hole 13 and the negative pressure sensor 19, there is provided an enlarged space 22. This space is provided as a collection place for dirt, contaminant, water drops, liquid medication, etc., preventing them from entering through the air hole 13 to adhere to the surface of the negative pressure sensor 19 to thereby cause it to malfunction.

At the opposite end of the air intake port 11, there is formed a mouthpiece outlet (inhaling port) 15 of a configuration adapted to be held in a human mouth. The mouthpiece outlet 15 has an elliptical sectional configuration in conformity with the configuration of a human mouth, and has a double structure in which there is provided a flow passage outlet 14 serving as the path for the liquid medication. The flow passage outlet 14 gradually increases in sectional area so that the mixture fluid consisting of air and the liquid medication may not spread abruptly at the outlet to adhere to the teeth, etc. in the mouth of the person holding the mouthpiece 15 in his or her mouth. Thus, when the user holds the mouthpiece 15 in his or her mouth, it is convenient for the end of the flow passage outlet 14 to be situated somewhat beyond the teeth. In order for this to be easily attained, the end of the flow passage outlet 14 may be formed so as to extend to the exterior somewhat beyond the end of the mouthpiece outlet 15. Further, as shown in FIGS. 1 and 6, the airflow passage of the mouthpiece 4 has a rectangular sectional configuration, so that when attaching the mouthpiece 4 in the housing, the attachment can be effected reliably, with the air intake port 11 being directed upwards.

Figure 11:
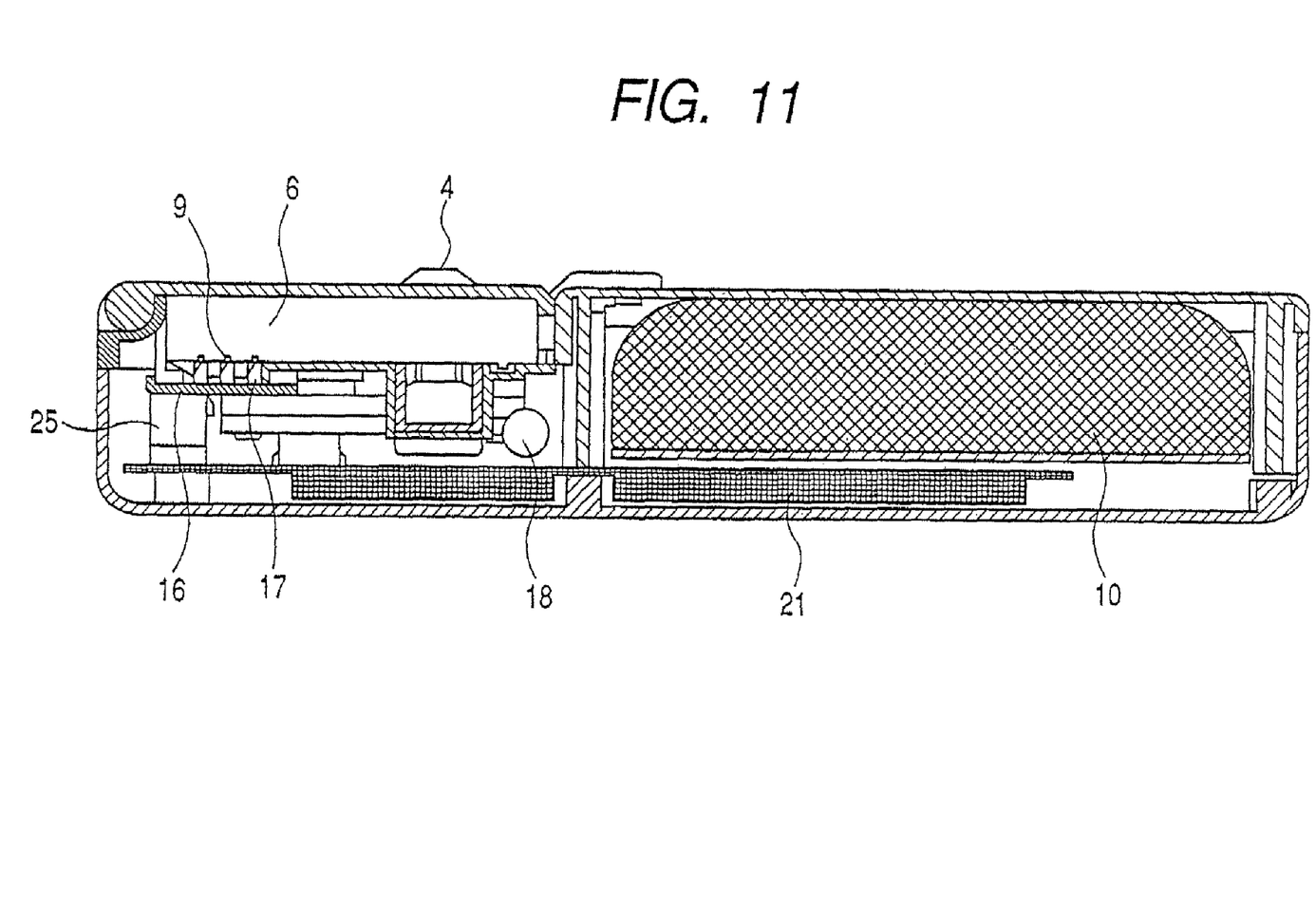
FIG. 11 is a general sectional view of the inhaler or inhaling device of FIG. 5.

FIG. 11 is an overall longitudinal sectional view of the inhaler of this application example. The control board 21 for controlling the inhaler is arranged under the battery 10. Further, a probe board 16 connected to the control board 21 by a cable or a connector (a connector 25 is used in the example of FIG. 11) is arranged under the CRG unit 6, and to effect connection between the probe board 16 and the electrical connection portion 9 of the CRG unit 6, a contact probe 17 for effecting heating energization of the head portion 8 of the CRG unit 6 is provided. In the space between the battery 10 and the mouthpiece 4, an oscillation motor 18 is arranged so as to be in contact with the control board 21.

The inhaling operation of this application example, constructed as described above, will be described with reference to FIG. 12.

When the patient (user) starts inhalation, and the negative pressure (related to the inhalation speed or the flow rate) detected by the negative pressure sensor 19 attains a range allowing discharge, liquid medication discharge is started at the head portion 8 of the CRG unit 6 through control by the control board 21. At the same time, the oscillation of the oscillation motor 18 is also started, informing the patient (user) of the start of liquid medication discharge. After the completion of liquid medication discharge in a predetermined amount from the head portion 8, in order that the last droplets of discharged liquid medication may reach the lungs, based on the inhalation speed and inhalation continuation time computed from the negative pressure measurement value of the negative pressure sensor 19, the oscillation motor 18 oscillates for a period of time corresponding to a preliminary inhalation after the completion of the discharge in order to effect inhalation in an amount corresponding to preliminary inhalation, urging the user to inhale so that the discharged liquid medication may reach the lungs. When the oscillation of the oscillation motor 18 is completed, the patient (user) stops inhalation. Due to this arrangement, the liquid medication discharge and inhalation are effected in synchronism with each other, making it possible to reliably send the liquid medication into the lungs and to eliminate failure such as deficient inhalation.

In this way, air enters the mouthpiece 4 through the air intake port 11 through inhaling operation by the patient (user), and is mixed with the liquid medication discharged from the discharge port provided at the head portion 8 of the CRG unit 6 to become a mixture fluid, which heads for the mouthpiece outlet 15 of a configuration adapted to be held in a human mouth. At the mouthpiece outlet 13, leakage of the mixture fluid through the side ends of the mouth is prevented to reduce wasteful inhalation, and it is arranged so that the mixture fluid is not allowed to easily impinge upon an obstacle in the mouth, such as the teeth, enabling the liquid medication to be efficiently inhaled in the body of the user.

In this application example, an oscillation motor is provided since the oscillation obtained by an oscillation motor is preferred to sound, for the patient (user) does not wish the people around to know his or her using the inhaler and wishes to avoid bothering them by the sound. This enables the user to perform inhalation anywhere easily.

Figure 13:
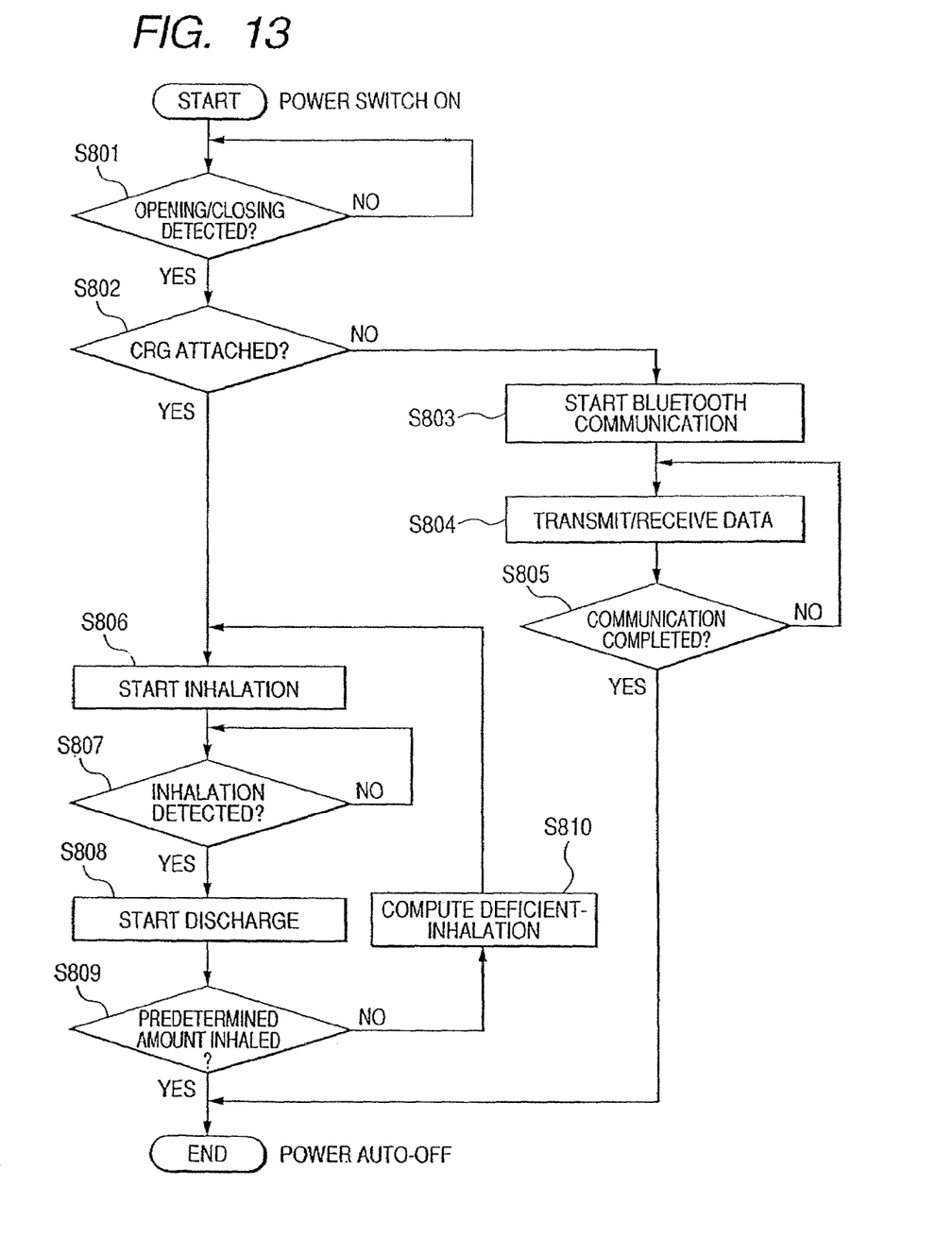
FIG. 13 is a flowchart illustrating the general operation of the inhaler or inhaling device of FIG. 5.

With reference to the flowchart of FIG. 13, an example of the general operation of the inhaler will be explained. When a power switch 101 is turned on, the opening/closing of the access cover 2 is detected (S801); when the access cover is open, a warning is issued through a display LED 102 or the like. When it is closed, a judgment is made as to whether the CRG unit 6 is attached or not (S802). In this example, when it is attached, bluetooth communication is started (S803), transmitting and receiving data regarding the patient (user), such as the dose (S804). With the completion of the communication (S805), the operation is completed. This mode is mainly employed by the doctor when he writes prescription information or checks the inhalation results up to that time.

When the CRG unit 6 is attached, the operation conducted is as follows. This mode is usually employed by the patient (user). When the patient (user) starts inhalation (S806), and this inhalation is detected and a fixed level of negative pressure is detected by the negative pressure sensor 19 (S807), the discharge head portion 8 starts droplet discharge (S808). When a fixed level of negative pressure is not detected, a warning may be issued to urge stronger inhalation.

From the start, the liquid medication discharge is continued for a predetermined period of time, discharging a predetermined amount of liquid medication. This amount is determined from the read data. Thereafter, the negative pressure sensor 19 monitors changes with the passage of time in the negative pressure due to the inhalation, and makes a judgment from the integration amount thereof (The point in time from which the integration amount is computed may be set appropriately) as to whether a predetermined amount of liquid medication has been inhaled or not (This integration amount is related to the amount of the mixture fluid composed of air and the liquid medication inhaled by the user, so that it corresponds to the detection of inhalation of a predetermined amount of liquid medication) (S809), the operation being completed upon inhalation of the predetermined amount of liquid medication. All this while, the oscillation of the oscillation motor 18 is effected. If, even after a predetermined period of time, the inhalation of the predetermined amount of liquid medication cannot be detected, a warning is given to the user through a change in the mode of oscillation of the oscillation motor 18, urging him to perform re-inhalation (S806). At this time, the deficient-inhalation amount is computed (S810), and, in accordance with the computation results, the amount of liquid droplets discharged by the discharge head portion 8, the inhalation time (that is, the oscillation time of the oscillation motor 18), etc. are set.

In the application example described above, the discharge port of the liquid medication discharge portion is reliably arranged at a position where there is generated a pressure difference smaller than the pressure difference from the atmospheric pressure detected by the pressure detecting portion at the time of inhalation, so that the possibility of liquid leakage through the discharge portion is reduced, and the adverse effect on the service life of the discharge portion is also reduced. And, it is possible to give a predetermined amount of liquid medication to the user reliably and efficiently through a simple operation.

APPLICATION EXAMPLE 2

Figure 14:
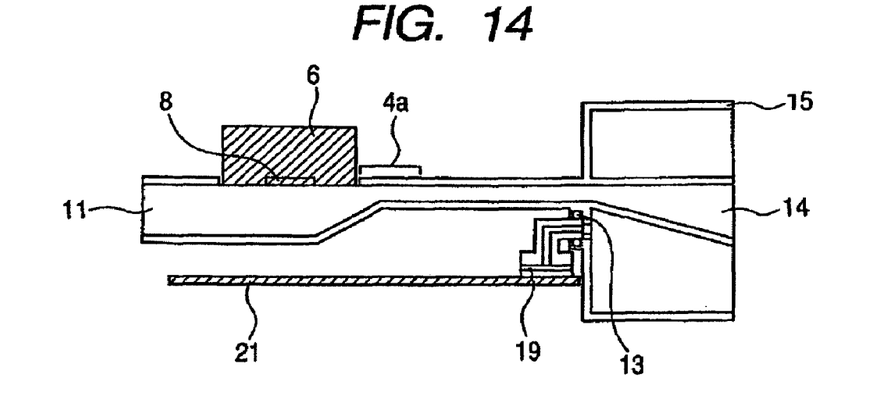
FIG. 14 is a sectional view showing the construction of a portion near the mouthpiece of a flow-passage-parallel type device of Application Example 2.

FIG. 14 shows Application Example 2, which solely differs from Application Example 1 in the construction of the flow passage to the pressure detecting portion (i.e., the communication hole 13 leading to the negative pressure sensor 19). In Application Example 2, the communication hole 13 is provided on the outer side of the flow passage outlet 14 of the mouthpiece outlet 15 at the forward end of the mouthpiece 4, whereby the negative pressure detecting flow passage leading to the negative pressure sensor 19 is completely separated from the air flow passage of the mouthpiece 4, and is arranged parallel thereto. When the attachment system in which the mouthpiece 4 is inserted from above and the front side of the inhaler is adopted, the attachment is effected in the direction in which the communication hole 13 is in intimate contact with the negative pressure detecting flow passage leading to the negative pressure sensor 19, which is advantageous in preventing air leakage. Thus, the negative pressure detection is effected reliably. Further, the negative pressure detecting flow passage leading to the negative pressure sensor 19 is completely separated from the flow passage for the liquid medication, so that the contamination due to the liquid medication, etc., of the negative pressure detecting flow passage is reduced, thereby securing highly accurate detection. Otherwise, this application example is the same as Application Example 1.

APPLICATION EXAMPLE 3

Figure 15A:
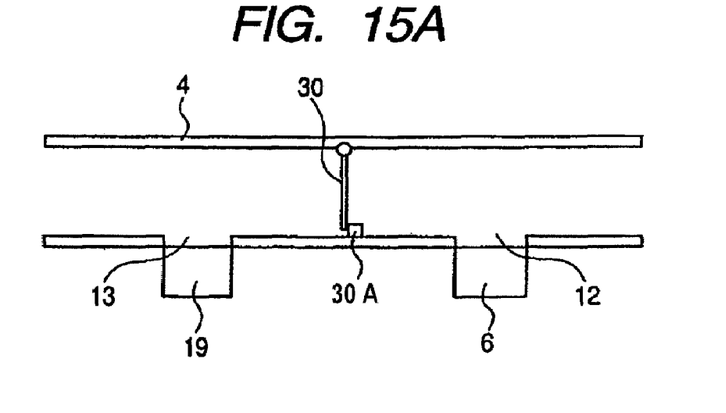
FIGS. 15A and 15B are diagrams illustrating the operation of Application Example 3, which uses a valve.
Figure 15B:
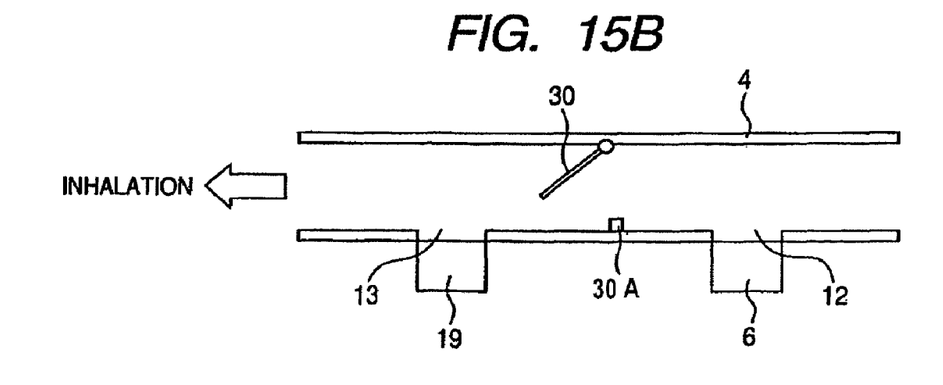

FIGS. 15A and 15B show Application Example 3, which is provided with a pressure mitigating means different from the flow passage throttle system of Application Example 1. In Application Example 3, in the flow passage of the mouthpiece 4, a valve 30 of substantially the same size as the sectional area of the flow passage is rotatably provided in the portion between the communication hole 13 leading to the negative pressure sensor 19 and the liquid medication intake port 12 of the discharge head portion 8. Except during inhalation, the valve 30 is normally in the state shown in FIG. 15A, in which it abuts a valve stopper 30a to substantially block the flow passage. When the user performs inhalation, the valve 30 opens as shown in FIG. 15B. In this process, a relatively high negative pressure is generated in the flow passage space on the negative pressure sensor 19 side, whereas no such high negative pressure is generated in the flow passage space on the discharge head 8 side. Thus, the same effect as that of Application Example 1 is obtained. Otherwise, this application example is the same as Application Example 1.

This application claims priority from Japanese Patent Application No. 2004-225510 filed on Aug. 2, 2004, which is hereby incorporated by reference herein.

What is claimed is:

1. A liquid medication cartridge comprising:
   an accommodating portion for accommodating a liquid medication;
   a liquid discharge portion having a discharge port for discharging the liquid medication by using an ink jet technique; and
   a communicating means for establishing communication between the accommodating portion and the liquid discharge portion,
   wherein said accommodating portion has a region which is cut off from the atmosphere by a first film and a second film, said region accommodating the liquid medication,
   wherein said communication means contains a liquid path for conducting the liquid medication from said accommodating portion to said liquid discharging portion and is formed as a unit with said liquid discharging portion, and
   wherein the cartridge is constructed to operate such that the communication between the liquid discharging portion and the accommodating portion is established when said communication means pierces said first film, then the liquid medication is filled in the liquid discharging portion when said communicating means further penetrates into said accommodating portion, then the region is communicated with the atmosphere when said communicating means pierces said second film.

2. A liquid medication cartridge according to claim 1, wherein the cartridge is constructed to operate such that the liquid overflows from the discharge port of said liquid discharge portion at a rate corresponding to 15% or more of the volume of the region in said accommodation portion when filling the liquid discharge portion with the liquid contained in the accommodation portion.

3. A liquid medication cartridge comprising:
   an accommodating portion for accommodating a liquid medication;

a liquid discharging portion having a discharge port for discharging the liquid medication by using an ink jet technique; and a communicating means for establishing communication between the accommodating portion and the liquid discharge portion, wherein said accommodating portion has a region which is cut off from the atmosphere by a film and a thin plate, said region accommodating the liquid medication, wherein said communicating means contains a liquid path for conducting the liquid medication from said accommodating portion to said liquid discharging portion and is formed as a unit with said liquid discharging portion, and wherein the cartridge is constructed to operate such that the communication between the liquid discharging portion and the accommodating portion is established when said communicating means pierces said film, then the liquid medication is filled in the liquid discharging portion when said communicating means further penetrates into said accommodating portion, and then the region is communicated with the atmosphere when said communicating means detaches said thin plate.

4. A liquid medication cartridge according to claim 3, wherein the cartridge is constructed to operate such that the liquid overflows from the discharge port of said liquid discharge portion at a rate corresponding to 15% or more of the volume of the region in said accommodating portion when filling the liquid discharge portion with the liquid contained in the accommodating portion.

* * * * *